United States Patent [19]

Collins et al.

[11] Patent Number: 4,476,434

[45] Date of Patent: Oct. 9, 1984

[54] NON-DESTRUCTIVE TESTING METHOD AND APPARATUS UTILIZING PHASE MULTIPLICATION HOLOGRAPHY

[75] Inventors: H. Dale Collins, Richland; James M. Prince, Kennewick; Thomas J. Davis, Richland, all of Wash.

[73] Assignee: The United States of America as represented by the United States Department of Energy, Washington, D.C.

[21] Appl. No.: 342,431

[22] Filed: Jan. 25, 1982

[51] Int. Cl.³ .................... G01R 33/12; G01N 27/72
[52] U.S. Cl. .................................. 324/233; 324/226; 324/262
[58] Field of Search .............. 324/233, 239, 338, 339, 324/226, 262; 73/602, 603; 367/7, 8, 11, 73

[56] References Cited

U.S. PATENT DOCUMENTS

| | | | |
|---|---|---|---|
| 3,159,784 | 12/1964 | Haslett et al. | 324/233 |
| 3,229,198 | 1/1966 | Libby | 324/240 |
| 3,302,105 | 1/1967 | Libby et al. | 324/233 |
| 3,314,006 | 4/1967 | Hentschel | 324/233 |
| 3,678,452 | 7/1972 | Silverman | 340/3 R |
| 3,721,876 | 3/1973 | Mori et al. | 324/233 |
| 3,872,380 | 3/1975 | Gardiner | 324/239 |
| 3,904,957 | 9/1977 | Griese | 324/238 |
| 4,004,216 | 1/1977 | Natens et al. | 324/233 |
| 4,005,358 | 1/1977 | Foher | 324/244 |
| 4,006,407 | 2/1977 | Flaherty et al. | 324/233 |
| 4,078,201 | 3/1978 | Buser | 324/233 |
| 4,084,136 | 4/1978 | Libby et al. | 324/238 |
| 4,093,382 | 6/1978 | Kurtz | 356/72 |
| 4,207,520 | 6/1980 | Flora et al. | 324/238 |
| 4,222,273 | 9/1980 | Tahahashi et al. | 73/603 |
| 4,250,451 | 2/1981 | Slagle | 324/239 |

OTHER PUBLICATIONS

Hildebrand et al., "Holography by Scanning" 1/1969, Journal of the Optical Society of America, vol. 59, No. 1, pp. 1-5.

*Primary Examiner*—Gerard R. Strecker
*Assistant Examiner*—Walter E. Snow
*Attorney, Agent, or Firm*—Robert Southworth, III; Richard E. Constant; Michael F. Esposito

[57] ABSTRACT

An apparatus and method for imaging of structural characteristics in test objects using radiation amenable to coherent signal processing methods. Frequency and phase multiplication of received flaw signals is used to simulate a test wavelength at least one to two orders of magnitude smaller than the actual wavelength. The apparent reduction in wavelength between the illumination and recording radiation performs a frequency translation hologram. The hologram constructed with a high synthetic frequency and flaw phase multiplication is similar to a conventional acoustic hologram construction at the high frequency.

8 Claims, 30 Drawing Figures

NON-DESTRUCTIVE TESTING METHOD AND APPARATUS UTILIZING PHASE MULTIPLICATION HOLOGRAPHY

The United States government has rights in this invention pursuant to Contract No. AT(45-1)-1830 between the U.S. Department of Energy and Battelle Memorial Institute.

BACKGROUND OF THE INVENTION

The present invention relates generally to an apparatus and a method for nondestructive testing of objects, and more particularly to an apparatus and method for utilizing low frequency radiation in the production of fringe patterns or synthetic holograms which are capable of being reconstructed by holographic techniques.

This disclosure relates generally to nondestructive testing for identifying structural characteristics of an object by scanned holographic techniques using a known source of radiation, such as electromagnetic or acoustical radiation. While electromagnetic radiation and nondestructive eddy current techniques are used in the described illustrative embodiments of the invention, it will be understood by those skilled in this technical area that other forms of radiation can be substituted and are to be encompassed within the disclosure of this invention.

The principles of electromagnetic nondestructive testing are well known. Specifically, eddy currents are generated within an object to be inspected by induction from an adjacent coil by an alternating excitation current. Eddy currents then generate magnetic fields which couple to the coil at the same frequency as that of the excitation current, but which may be of a different phase. The phase and amplitude of the induced voltages depend upon the structural characteristics of the object under test. The phase relationships may be measured by appropriate signal processing circuits.

The flow of eddy currents in a test object is governed by the skin effect phenomenon. The currents decrease exponentially with depth, depending on the shape of the object, its thickness, and its electromagnetic properties. In addition to the decrease of current amplitude as depth below the surface increases, the phase angle of the current increasingly lags the excitation signal.

A detriment common to many eddy current test procedures is the inability to obtain sharp dimensional definition of flows or anomalies. When images are obtained, flaws in the object being tested are typically portrayed in a shapeless image or an image whose shape does not correlate to the shape of the flaw itself. This limitation arises from the long electromagnetic wavelengths required to obtain adequate penetration into the object. If wavelength is reduced by increasing the test frequency, eddy current penetration is likewise reduced because of the skin effect phenomonen. Furthermore, geometric limitations in the size of the available scanning aperture prevents imaging of flaws by holographic imaging processes when using such long wavelengths, since often only a single wavelength fringe circle is available with respect to a given point on the structural characteristics for imaging purposes. A single fringe circle from a point source is impossible to reconstruct optically because there exists no diffraction pattern or lens for holographic reconstruction purposes. Thus, an image of a point defect under these conditions is negated. This restricted aperture occurs in many applications where the defect is either near the surface or confined by geometry.

In the article titled "Holography by Scanning" by B. P. Hildebrand and Kenneth Haines, J. Opt. Soc. Am., Vol. 59, pages 1–19 (1969), there is a general discussion of the currently known techniques of imaging relating to scanned acoustic holography. The image location equations and magnifications discussed with respect to this disclosure were derived from a phase multiplication factor which appears to synthetically reduce the construction wavelength to simulate such previously known holographic techniques.

U.S. Pat. No. 4,084,136 to Libby et al discloses an eddy current testing device which produces a display of variations in characteristics of a sample. A signal expander samples a generated signal and expands the sample signal on a selected basis of square waves or Walsh functions to produce a plurality of signal components representative of the sampled signal. These are combined by a circuit network to provide a display of a defect. The initial signals are lissajou patterns which are then projected and rotated to provide a line image of a subsurface defect. While a visual display is achieved, an accurate representation of the size and dimensions of the detected flaw does not result.

In U.S. Pat. No. 3,721,896 to Mori et al, an eddy current testing technique is described in which the output signal from the object is processed to double the frequency and phase of the signal to produce a reference phase signal. The doubled reference phase is compared with a reference phase developed by a phase shifter to increase the sensitivity of a synchronous comparator. The system determines the difference between the two phases and results in a final output signal representing the detected difference. While this disclosure identifies the possibility of increasing the sensitivity of the eddy current testing technique, it contains no suggestion of utilizing such a signal to produce fringe patterns containing holographic information for further processing.

U.S. Pat. No. 4,005,358 to Foner discloses a magnetometer wherein distortions in the measured magnetic moment due to eddy currents are eliminated by the cancellation of out-of-phase signals through an alternating current feedback network. There is no discussion of potential phase multiplication or holographic imaging.

Another prior patent directed to the task of increasing information available from eddy current testing devices is U.S. Pat. No. 3,229,918 to Libby. The invention disclosed employed at test coil excited by a multi-frequency signal. The resulting outputs of the apparatus are analog signals representative of object characteristics. No imaging techniques are disclosed. Prior U.S. Pat. 4,207,520 to Flora et al describes an analog to digital type of balance system dealing with eddy current test techniques. Output signals are processed in a computer to provide phase sensitive detection of flaws such as cracks, but no imaging is discussed.

U.S. Pat. No. 3,678,452 to Silverman relates to acoustic holography and utilizes a frequency multiplier for increasing the described sampling techniques. This subdivides the coherent wave period into a number of phase integrals, each representative of a corresponding step in a final hologram parameter such as gray-scale density. Phase multiplication techinques for synthetically producing an image reproducable by holographic techniques are not discussed.

In U.S. Pat. No. 4,222,273 to Takahashi et al, there is described a holographic apparatus for detecting and imaging flaws in objects. A hologram is displayed in a fringe pattern and the position and shape of the object can be determined from that pattern by reproduction techniques. Frequency dividing techniques are used, but synthetic multiplication of detected phase signals is not described.

SUMMARY OF THE INVENTION

It is an object of this invention to provide an apparatus and method for synthetic aperture expansion in holographic imaging applications to construct fringe patterns capable of holographic reproduction where aperture restrictions in nondestructive testing applications would conventionally make such imaging techniques impossible.

A further object of the invention is to accomplish the production of such fringe patterns without increasing the frequency of the radiation directed to the test object, which would limit available penetration.

Another object is to synthetically produce fringe patterns from the measured test signals in a form which can be converted by holographic techniques into an accurate visual display of structural characteristics in a test object.

Another object is to provide a nondestructive test technique which can be employed with any form of radiation amenable to coherent signal processing methods. The technique results in permitting inspection of an object at a lower frequency with excellent depth penetration and a resulting image simulating that available at higher frequencies and producing excellent lateral resolution.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects and in accordance with the purposes of the present invention as embodied and broadly described herein, the apparatus of this invention may comprise scanning means for generating an output signal of constant frequency which varies in phase value as a function of the structural characteristics of the test object. A phase multiplier is utilized for multiplying the frequency and phase values of the output signal by a preselected number. A detector circuit detects phase differences between the multiplied output signal and a reference excitation signal whose frequency is also multiplied by the preselected number. The resuling signals are directed to a visual display for recording a scanned plot of the object as fringe patterns capable of being reconstructed by holographic techniques.

In a further aspect of the present invention, in accordance with its objects and purposes, the method hereof may also comprise the steps of penetrating a test object by radiation from an excitation signal of constant frequency, scanning the object to produce an output signal varying in phase value as a function of the structural characteristics of the object, multiplying the phase values and frequency of the output signal by preselected number, detecting phase differences between the multiplied phase values and the phase values of the excitation signal after its frequency is also muliplied by the same preselected number, and recording a scanned plot of the object as a function of the detected phase differences to produce fringe patterns which can be reconstructed by holographic techniques.

The apparatus and method result in the production of a sharply defined frontal image of structural characteristics which could not otherwise be imaged because they occur either near the surface of the object or are confined by geometry restricting aperture dimensions available for scanning purposes. The depth of the structural characteristic below the surface of the object can also be determined by the reconstruction parameters which produce the sharpest focus. Lateral resolution is established by simulated reduction in the radiation wavelength and may easily be an order of magnitude less than the electromagnetic wavelength in the material or 2 times the standard depth of penetration. Since the phase multiplication technique is performed on the detected data, the penetration depth available due to the longer wavelength signals applied to the test object remains unchanged. The phase multiplication technique can also be applied to low frequency acoustic holography, resulting in a test which combines excellent penetration of difficult materials with high resolution images.

It will be understood that the previously known techniques of electromagnetic testing and acoustical holography and those of the present invention whose description is to follow do not depend on the particular wave radiation utilized. The invention is applicable to the entire spectrum of electromagnetic radiation, including visible light, microwaves, infrared, ultraviolet, X-rays, radio waves, etc., and for all ranges of compressional or acoustic radiation. It applies to coherent imaging and to noncoherent imaging techniques using holographic time of flight phase computation processes. The synthetically developed holograms or fringe patterns which result from this invention contain holographic information capable of being processed by the use of coherent light to result in a visual image of the structural characteristics of the object under test.

BRIEF DESCRIPTION OF THE DRAWINGS

The accompanying drawings, which are incorporated and form a part of the specification, illustrate several embodiments of the present invention and, together with the description, serve to explain the principles of the inventions. In the drawings.

DETAILED DESCRIPTION OF THE INVENTION

Reference will now be made in detail to the present preferred embodiments of the invention, examples of which are illustrated in the accompanying drawings.

When used for electromagnetic non-destructive testing purposes, eddy currents are caused to flow within an object to be tested by induction from an adjacent coil which is excited by an alternating current. The eddy currents generate magnetic fields which couple to the receiver coil and induce voltages within the receiver coil which are at the same frequency as that of the excitation current applied to the sender coil, but which may be of a different phase angle. The phase angle and amplitude of the induced voltages depend upon the characteristics of the object under test. The induced voltage may be measured by suitable electronic equipment which senses either a variation in voltage (two coil method) or equivalent impedance of the coil (single coil method).

A detriment common to many eddy current tests is the inability to obtain sharp dimensional definition of flaws or anomalies. The restricted available aperture dimensions where the flaw or anomoly is either near the surface of an object or is otherwise confined by geometry makes imaging impossible because recorded fringe patterns do not include multiple fringes to produce a usable diffraction pattern or lens.

The invention disclosed herein presents a solution to this problem in that the effective wavelength can be synthetically reduced by one or two orders of magnitude by manipulation of the sensed output signals. Since the output signals are manipulated, the technique preserves the available degree of penetration available by use of longer test frequencies. The result is the ability to generate high resolution images of flaws or anomolies using image reconstruction techniques where such imaging is otherwise impossible.

Frequency and phase multiplication of the received flaw signals appears to synthetically reduce the construction or test wavelength by the multiplication factor. The apparent reduction in wavelength performs a synthetic frequency hologram. The resulting fringe patterns constructed with the high synthetic frequency are similar to those found in a hologram of the same frequency. This concept allows inspection of objects at lower test frequencies with excellent depth penetration and results in the production of reconstructed images at the higher synthetic frequency with increased magnification and resolution. This permits the use of the technique for the quantification, classification and high resolution imaging of flaws and anomalies using eddy current or acoustic data.

Figure 1:
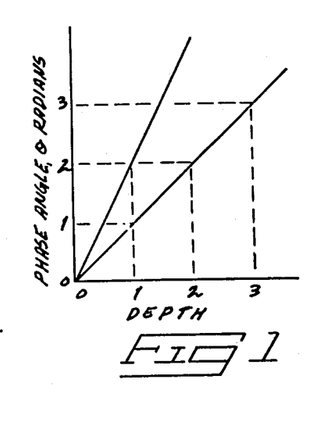
FIG. 1 is a plot of eddy current phase angles as a function of depth.

The flow of eddy current in a test object is governed by the skin effect phenomenon. The currents decrease exponentially with depth, and the phase angle of the current increasingly lags the excitation signal. The normal linear and phase multiplied relationships between depth and phase angle in the idealized plane wave case is shown in FIG. 1. The phase angle is seen to increase with object depth. This one parameter is utilized to construct the display of fringe patterns according to this invention.

According to the present method, the object being tested is first penetrated by waveform radiation from an excitation signal of constant frequency. When using electromagnetic processes, the frequency source is an oscillator having an excitation signal fed to a coil. The object is then scanned to produce an output signal at the constant frequency. The phase angle of the output signal will vary as a function of structural characteristics encountered in the object.

In eddy current applications, the object will be scanned by a scan coil. The phase values and frequency of the output signal from the scanning device or scan coil is then multiplied by a preselected number to synthetically reduce the signal wavelength. Phase differences in the scanning plane are then detected between the multiplied phase values of the output signal at the multiplied frequency and phase values of the similarly multiplied frequency of the excitation signal. The detection of these phase value differences as points about the object are scanned is used to produce a scanned plot of the object as a functin of the detected phase differences. This produces fringe patterns capable of being reconstructed by holographic techniques as a visual image of the structural characteristics of the object.

In a preferred embodiment, the recording step is accomplished on a recording oscilloscope. The detected phase differences are used as a write signal to control display on the oscilloscope screen in conjunction with two dimensional scanning coupled to usual operation of the scan coil.

Figure 2:
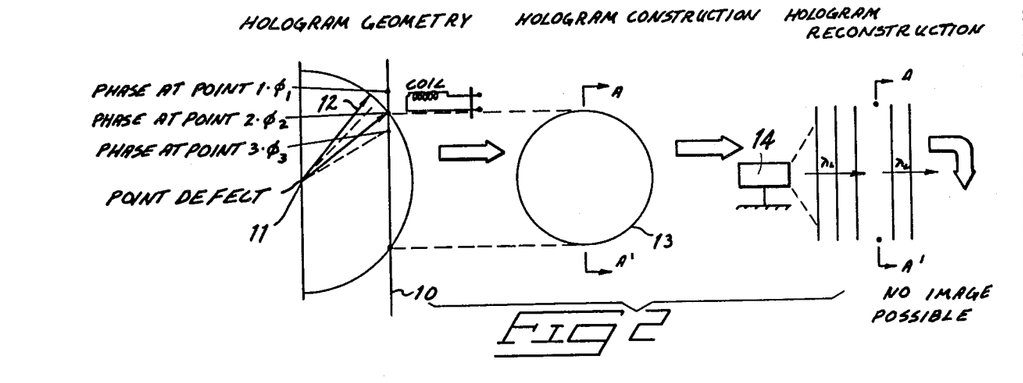
FIG. 2 is a schmetic diagram illustrating the problem of aperture limitations and resulting failure to produce fringe patterns capable of developing an image.
Figure 3:
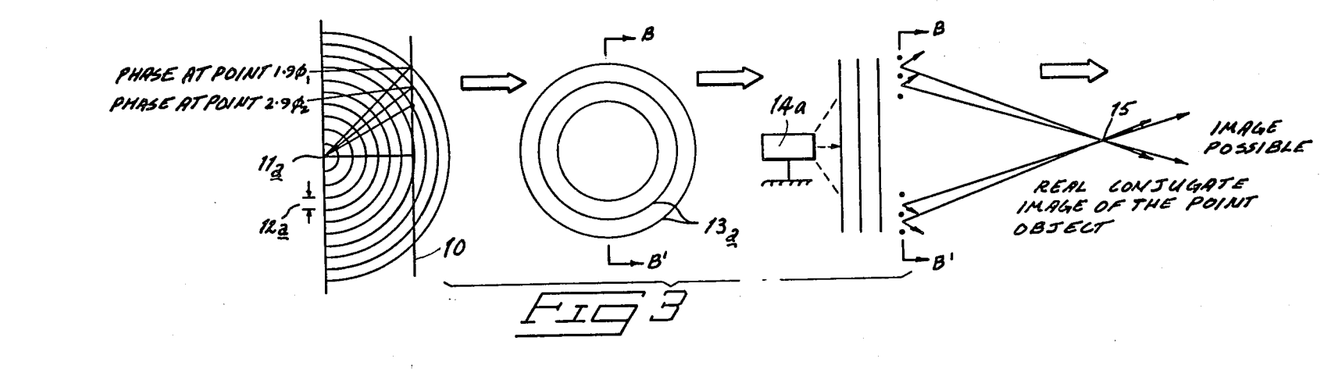
FIG. 3 is a similar diagram illustrating the technique of the present process.

FIG. 2 illustrates the sequence of events that occur in constructing fringe patterns under prior art restrictions as to depth and aperture dimensions. FIG. 3 similarly illustrates the steps utilized in the present method.

FIG. 2 illustrates eddy current coil scanning along a scanning plane 10 across a point defect 11. The length of the applied wavelength is shown by the line 12. The resulting fringe pattern 13 comprises a two dimensional one fringe circle. The single fringe limitation is due to the scanned aperture dimensions being insufficient to produce a multi-fringe hologram that can be reconstructed. This restricted aperture limitation occurs in many applications where the defect is either near the surface or confined by equipment geometry. When subjected to coherent light from a laser 14, using conventional holographic techniques, no image can be produced from such a single fringe pattern.

FIG. 3 similarly illustrates the result when the phase angles and output signal frequency of the scanned output signal are multiplied by a preselected number. The example chosen is a multiplication factor of nine. The wavelength between the illustrated concentric circles emanating from point defect 11a is now one ninth that shown in FIG. 2. Multiple fringes 13a are produced across the same scanning plane 10 when viewing the same point defect 11a. The synthetic reduced wavelength is shown by the line 12a. Now, when the image containing the multiple fringes 13a is illuminated by laser 14a, a real conjugate image of the point object is achieved at 15.

According to this invention, all phase values obtained in the conventional general approach schematically shown in FIG. 2 are synthetically multiplied by an arbitrary expansion factor. Multiplying the phase values produces a new expanded aperture hologram with the typical multi-fringe or zone lens pattern that is so familiar in acoustic holography. Thus, through synthetic wavelength reduction it is possible to construct a unique two dimensional image of defects detected by eddy current or other waveform radiation scanning techniques.

Figure 4:
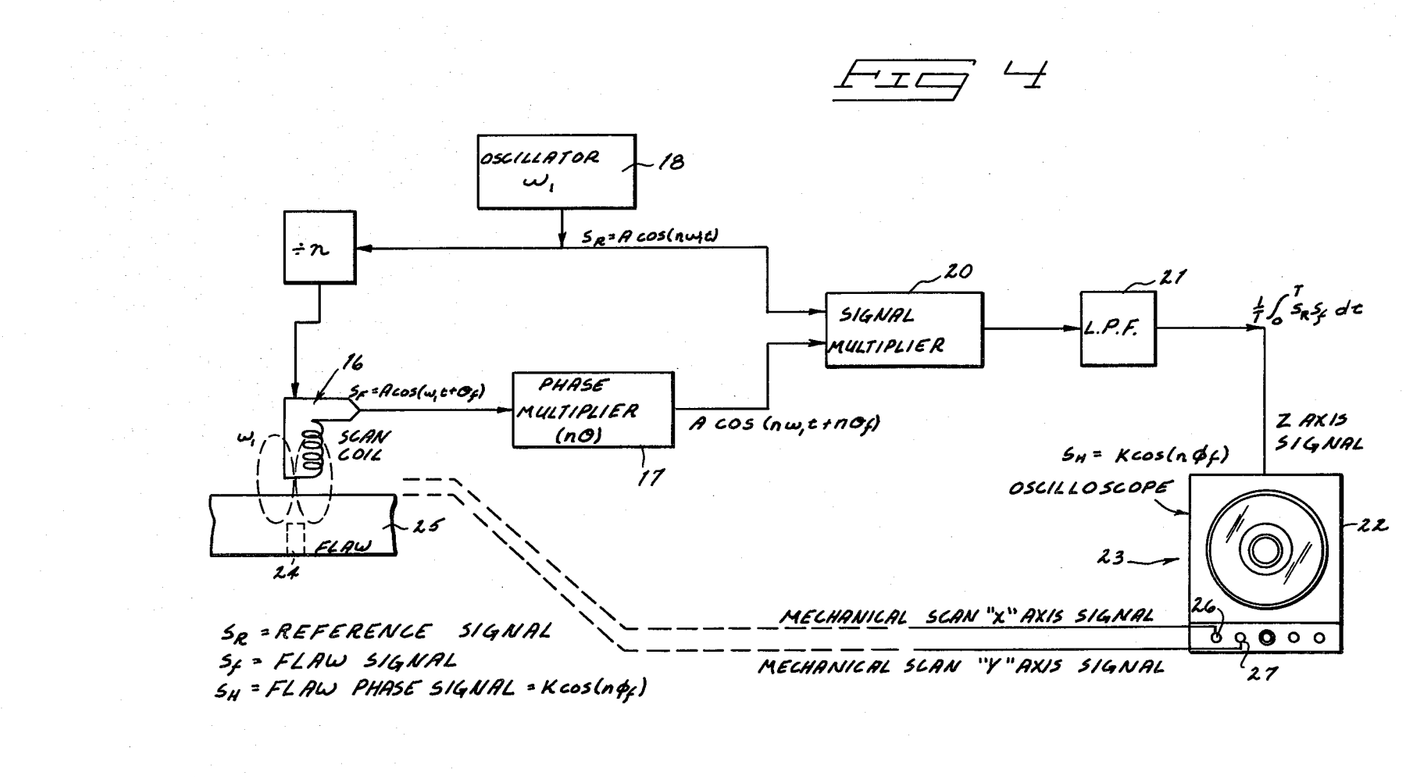
FIG. 4 is a simplified block diagram of an eddy current system according to this invention.

The simplified block diagram of FIG. 4 shows an exemplary apparatus for implementing the above described method for eddy current testing. The scanning coil 16 is excited at a test frequency of ($\omega_1$). Any off-null or flaw signal from the eddy current bridge is applied to a phase multiplier 17. The flaw signal is represented by the symbol $S_f$.

Both the frequency and phase of the flaw signal, $S_f$, are multiplied by a preselectable number (n) in the phase multiplier 17. The phase of the resulting signal is then detected with respect to a reference signal from the excitation oscillator 18 of the same frequency ($n\omega_1$). The reference signal is designated in FIG. 4 as $S_R$. The detected phase information from the phase detector comprising signal multiplier 20 and a low pass filter 21 is a flaw phase signal designated in FIG. 4 as $S_H$. The flaw phase signal is utilized as a write command on a storage oscilloscope 22.

Movement of the scan coil 16 is coupled to the oscilloscope 22 through the usual mechanical scan access signal inputs 26 and 27. A pattern similar to a hologram and consisting of a unique set of fringe patterns 23 will be written on the display as a flaw 24 is scanned in an object 25.

In general, the testing apparatus preferably includes scanning means, illustrated as scan coil 16, for generating an output signal (flaw signal $S_f$) of constant frequency which varies in phase value as a function of the structural characteristics of object 25, specifically detection of flaw 24. Phase multiplier means, shown generally at 17, is utilized for multiplying the frequency and phase values of the flaw signal $S_f$ by a preselected number (n). Means is provided for detecting phase differences between the multiplied output signal or flaw signal $S_f$ and a reference excitation signal or reference signal $S_R$ which equals the scanning frequency multiplied by the factor applied to the flaw signal. The multiplied frequencies are processed by means responsive to the detection of such phase differences for recording a scanned plot of the object 25 as fringe patterns 23. This is shown as oscilloscope 22, which has its write command controls operably connected to the phase detector comprised of signal multiplier 20 and low pass filter 21. The resulting fringe patterns 23 are capable of being reconstructed by holographic techniques, such as the optical system shown to the right in FIG. 3. Such reconstruction results in production of a visual image of the structural characteristics or flaw 24 detected in the object 25.

The following mathematical discussion presents an analysis of phase multiplication holography employing simultaneous focus (or point) source-receiver scanning. The analysis used is similar to that utilized in the publication of Hildebrand and Haines referred to in the "Background of the Invention". The image location equations are derived for the various scanning techniques that are used in phase multiplication holography.

Figure 5:
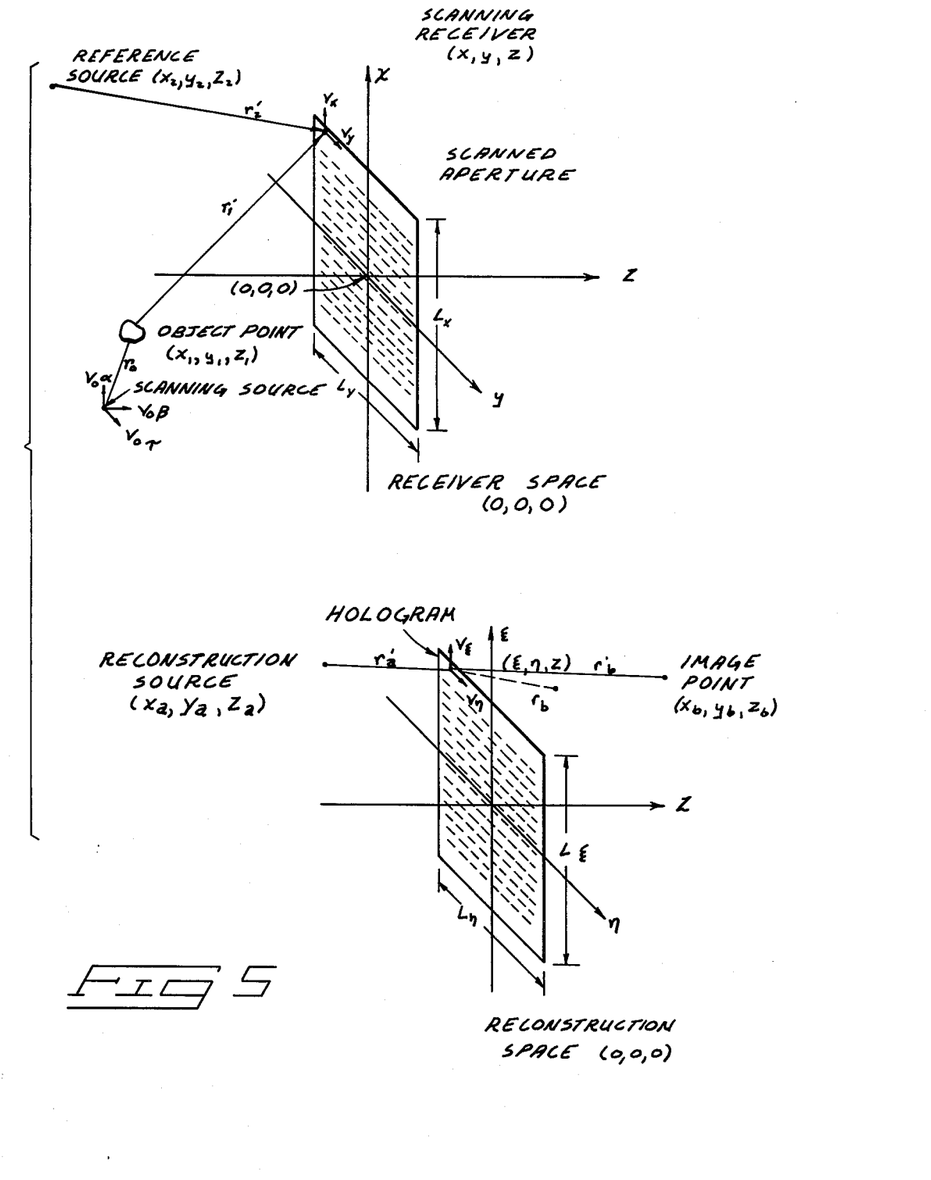
FIG. 5 is a schematic view illustrating the construction and reconstruction geometry used in analyzing the technique.

The synthetic hologram construction and reconstruction geometry used in the analysis is illustrated in FIG. 5. The phase at the receiver point (x,y,z) during the synthetic hologram construction is $$\phi(x,y,z) = \phi_0(x,y,z) - \phi_r(x,y,z) \qquad (1)$$

and $$\phi(x,y,z) = \frac{2\pi n}{\lambda_S} [r_0' + r_1' - r_2'] \qquad (2)$$

The phase at the receiver point (x, y, z) after illumination of the synthetic hologram by the reconstruction source is $$\phi_1(x,y,z) = \pm \frac{2\pi n}{\lambda_S} [r_0' + r_1' - r_2'] - \frac{2\pi}{\lambda_L} r_a' \qquad (3)$$

where
n = phase multiplication factor
  = construction wavelength
  = reconstruction wavelength
+ refers to the conjugate image
− refers to the true image If the phase from Eq. (2) is to focus at the image point ($x_b, y_b, z_b$), then $$\phi_1(x,y,z) = \frac{2\pi}{\lambda_L} r_b' \qquad (4)$$

which is termed the Gaussian-image sphere. The usual procedure is to expand the distance terms ($r_a'$, $r_b'$, $r_1'$, $r_2'$ and $r_0'$) in a binomial series and equate coefficients of x, y and z. We expand the distance terms about the origin of the (x, y, z) system and the distance $r_0$ is expanded about the $\alpha, \beta, \gamma$ system. The area in which the receiver scans is assumed small with respect to the distance and is centered at the (x, y, z) origin. A similar restriction holds for the source motion. The first order terms yield the Gaussian image location equations:

$$\frac{1}{r_b} = \pm \frac{n}{m^2} \frac{\lambda_L}{\lambda_S} \frac{1}{r_1} + \frac{1}{r_0} - \frac{1}{r_a} \quad (5)$$

$$\frac{x_b}{r_b} = \pm \frac{n}{m} \frac{\lambda_L}{\lambda_S} \left( \frac{x_1}{r_1} + \frac{(x_1 - x_0)}{r_0} \right) - \frac{x_a}{r_a} \quad (6)$$

$$\frac{y_b}{r_b} = \pm \frac{n}{m} \frac{\lambda_L}{\lambda_S} \left( \frac{y_1}{r_1} + \frac{(y_1 - y_0)}{r_0} \right) - \frac{y_a}{r_a} \quad (7)$$

where $r_2 = \infty$ (plane wave reference beam) and the synthetic hologram magnification $m = m_x = m_y$.

If we assume simultaneous source-receiver scanning configuration, the approximate image-to-phasogram distance is given by Eq. (8).

$$r_b = \frac{\lambda_S}{n} \frac{m^2}{\lambda_L} \frac{r_1}{2} \quad (8)$$

The synthetic hologram appears to have been constructed at the smaller synthetic wavelength (i.e., $\lambda_{S/n}$). This reduces the effective distance by $1/n$ as compared with a hologram constructed with $\lambda_S$. The synthetic hologram will have the same image distance as a hologram constructed with the equivalent $\lambda_{S/n}$ wavelength. The synthetic hologram constructed at the lower frequency simulates a higher frequency hologram.

The lateral image magnification for the same scanning configuration is easily derived from the image locations equations and is given by Eq. (9). The image magnification is effectively $$M_L = \frac{2\lambda_L}{\lambda_{S/n}} \left( \frac{1}{m} \right) \frac{r_b}{r_1} \quad (9)$$

This analysis mathematically substantiates the construction of a synthetic frequency translation hologram by use of the present technique. It verifies the experimental procedures discussed below.

Figure 6:
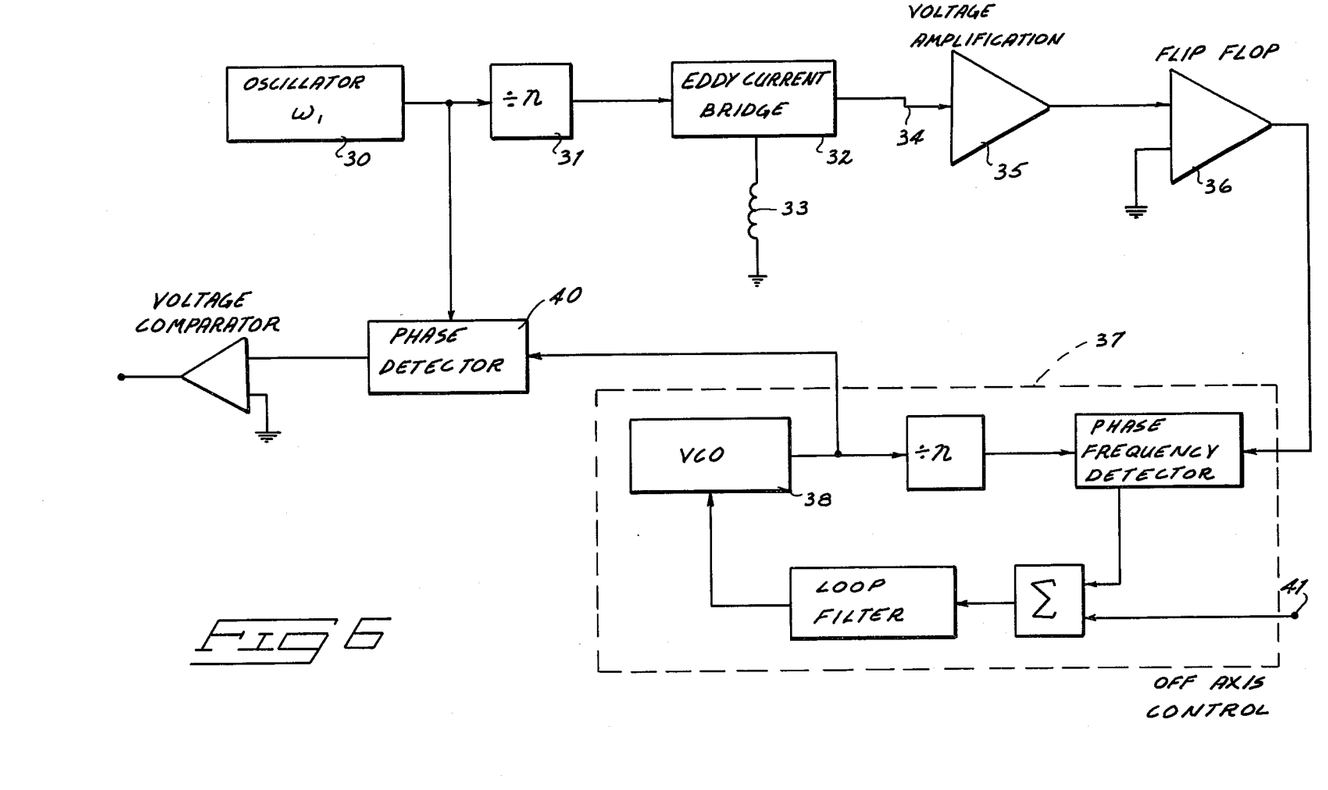
FIG. 6 is a block diagram of an illustrative circuit for carrying out the invention.
Figure 7:
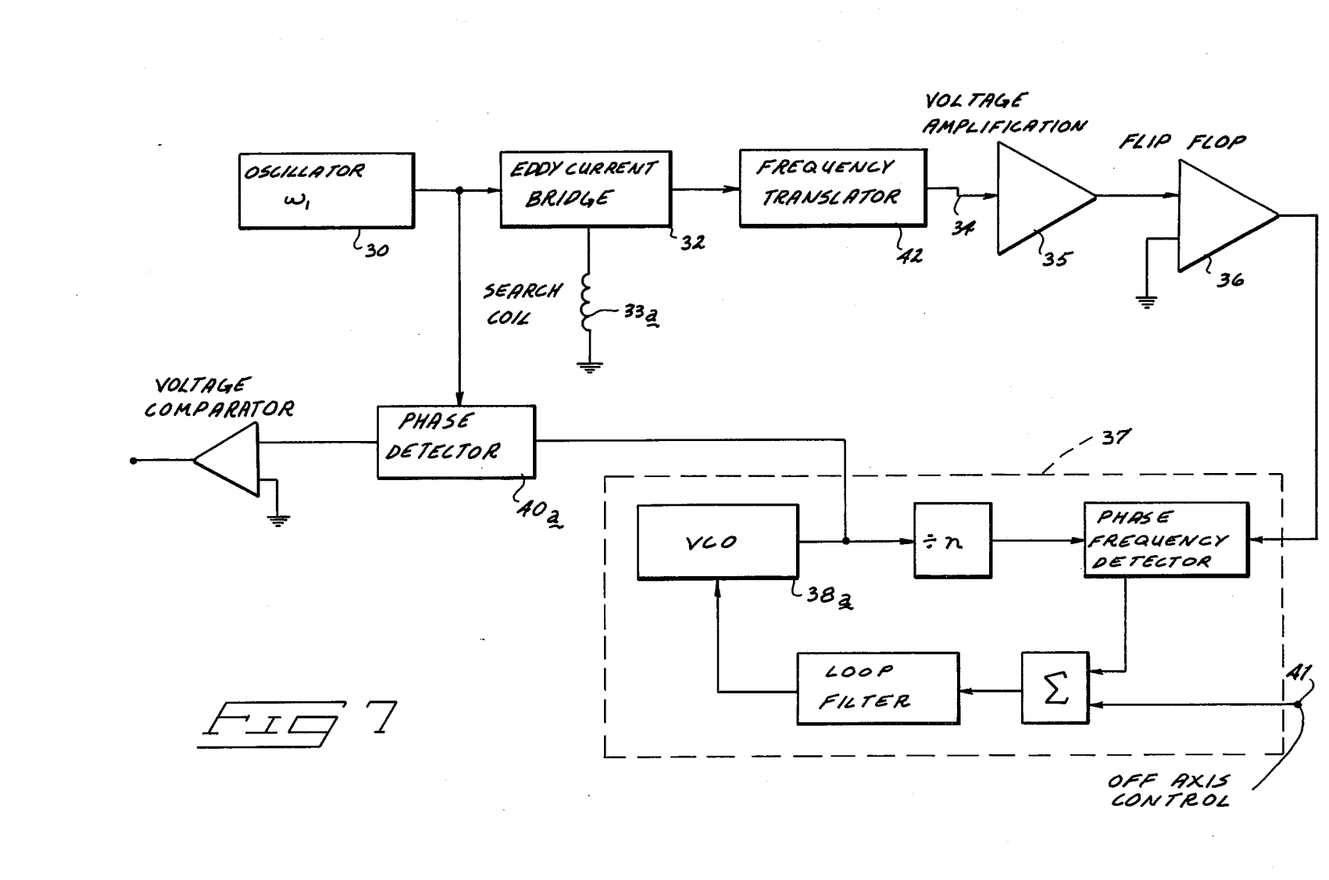
FIG. 7 is a block diagram of a modified circuit.

Two general methods for implementing the phase multiplication process for generating holograms are shown in FIGS. 6 and 7. In the method shown in FIG. 6, a test frequency of $\omega_1$ is obtained from an excitation oscillator 30 and a drive-by-n counter 31. The test frequency is applied to conventional eddy current electronics shown as an eddy current bridge 32 and search coil 33. Off balance signals from the eddy current bridge 32, graphically shown at 34, are amplified in a suitable amplifier 35. They are squared by a zero crossing detector 36 and used as a reference frequency for a phase locked loop 37. The phase multiplication is performed by the phase locked loop 37. Both the frequency and phase of the voltage controlled oscillator 38 included within the loop will be n times that of the frequency and phase of the signal applied to search coil 33. The voltage controlled oscillator output is applied to a phase detector 40 whose reference frequency is applied from oscillator 30 is $n\omega_1$. The preferred embodiment for the phase detector 40 is an exclusive or logic gate whose output is low pass filtered. The phase detector output is used as a Z-access write command for the display device or oscilloscope (not shown).

A provision is made within the phase locked loop 37 for obtaining the equivalent of an off-axis reference signal at 41. This aids the optical image reconstruction process by spatially separating the zero order light from the diffracted image. A phase lag is introduced into the voltage controlled oscillator 38 which is a linear function of the voltage applied to the off-axis control input.

A second and more advantageous method of hologram generation is shown schematically in FIG. 7. This method uses frequency translation of the coil 33a to an intermediate frequency which is $1/n$ times the test frequency ($\omega_1$). The frequency is divided by the preselected number n by means of a frequency translator shown at 42. The remaining components shown schematically in FIG. 7 are numbered to correspond with the elements illustrated in FIG. 6. Frequency translation of the coil signal is extremely beneficial since the final phase detector 40a and the voltage controlled oscillator 38a can be operated at the test frequency ($\omega_2$) rather than at a multiple of the test frequency ($n\omega_1$). If, for example, a test frequency of 1 Mhz and a multiplication (n) of 40 were used, a voltage controlled oscillator 38 in FIG. 6 would have to operate at 40 Mhz. The arrangement shown in FIG. 7 alleviates the need for the rigorous design of these high frequency circuits.

One method for implementing the frequency translation required in conjunction with the technique of FIG. 7 is single sideband suppressed carrier amplitude modulation. Both amplitude and phase of the high frequency signal are preserved in the lower sideband or difference frequency. Another method involves detecting the in-phase and quadrature amplitude coefficient of the bridge signal (Fourier amplitude coefficience) and using these levels to control the amplitude of a sine and cosine wave respectively at the lower intermediate frequency. When these two waves are summed together, the result is an intermediate frequency sinusoid having the phase and amplitude characteristics of the bridge signal.

As an example of the circuit parameters employed, one of our applications used a test frequency of 400 kHz and a phase multiplication factor equal to 40. The intermediate frequency was thus 10 kHz, permitting the voltage controlled oscillator 38a and phase detector 40a (FIG. 7) to operate at the original test frequency.

Figure 8:
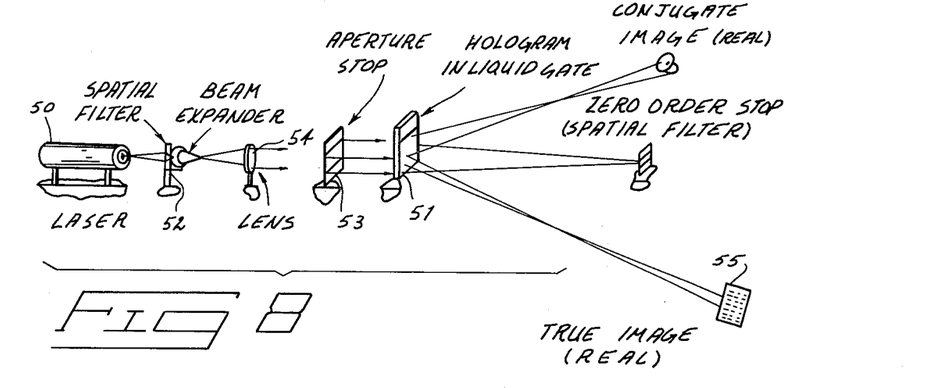
FIG. 8 is a schematic view of an optical reconstruction system for use in conjunction with the present disclosure.
Figure 9:
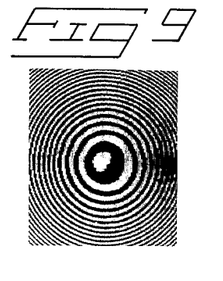
FIG. 9 is a photograph of the fringe patterns obtained as a result of this invention.
Figure 10:
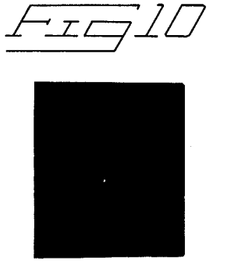
FIG. 10 is a reconstruction of a point image from the fringe patterns shown in FIG. 9.
Figure 11:
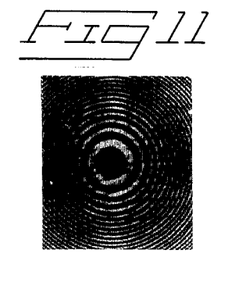
FIGS. 11 and 13 are photographic of reference holograms.
Figure 12:
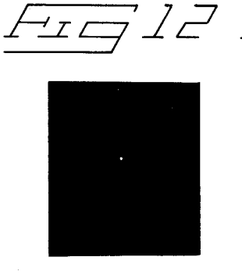
FIGS. 12 and 14 are images corresponding to the fringe patterns in FIGS. 11 and 13, respectively.
Figure 13:
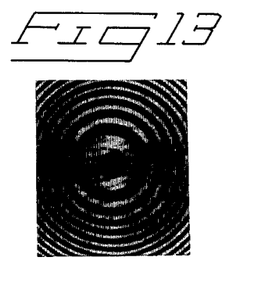
Figure 14:
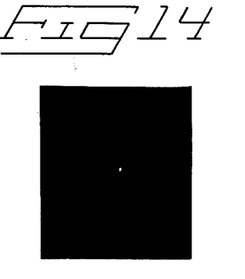
Figure 15:
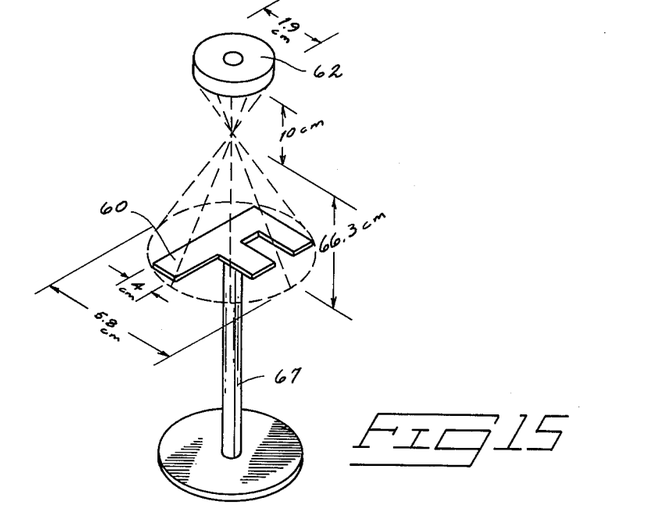
FIG. 15 is a schematic representation of the construction geometry used in verifying the present techniques.
Figure 16:
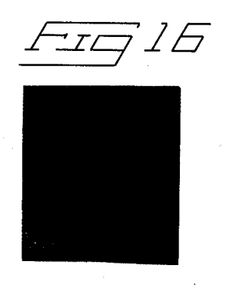
FIG. 16 is a photograph of the fringe patterns obtained as a result of the experiments illustrated in FIG. 15.
Figure 17:
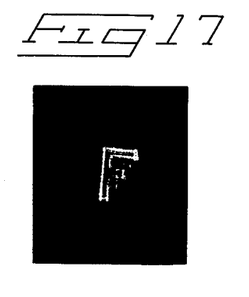
FIG. 17 is a reconstructed image developed from the fringe patterns in FIG. 16.
Figure 18:
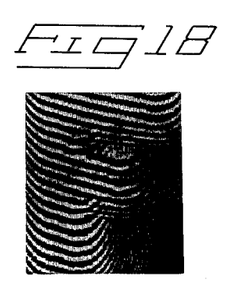
FIGS. 18 and 20 are photographs of reference acoustical holograms.
Figure 19:
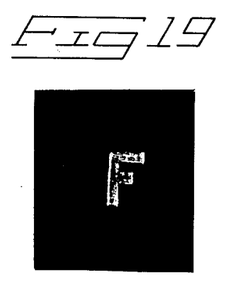
FIGS. 19 and 21 are images constructed from the fringe patterns of FIGS. 18 and 20, respectively.
Figure 20:
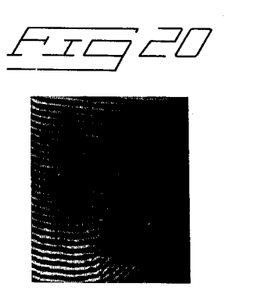
Figure 21:
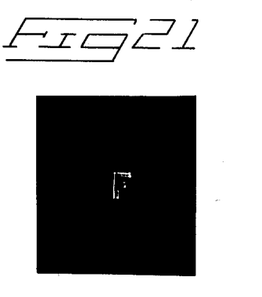
Figure 22:
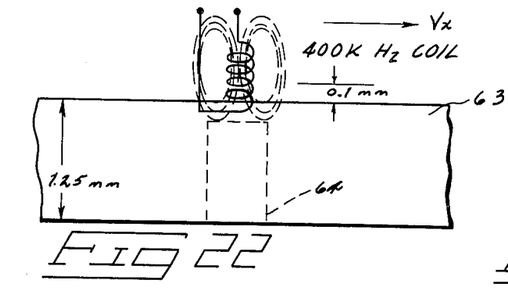
FIG. 22 is a schematic plan view of a test procedure utilizing the present technique.
Figure 23:
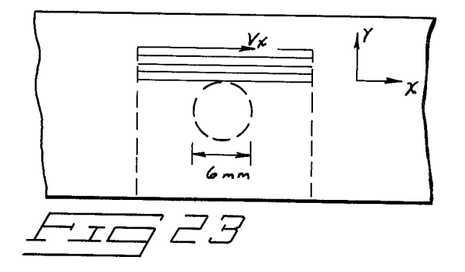
FIG. 23 is a plan view of the test procedure in FIG. 22.
Figure 24:
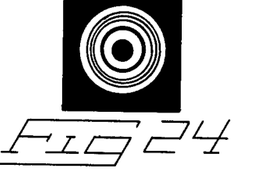
FIG. 24 illustrates the fringe patterns which resulted from the test procedure shown in FIGS. 22 and 23.
Figure 25:
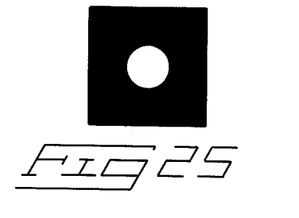
FIG. 25 is a reconstructed image developed from the fringe patterns of FIG. 24.
Figure 26:
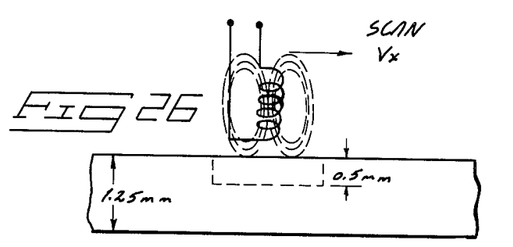
FIG. 26 is a schematic plan view of a test procedure utilizing the present technique.
Figure 27:
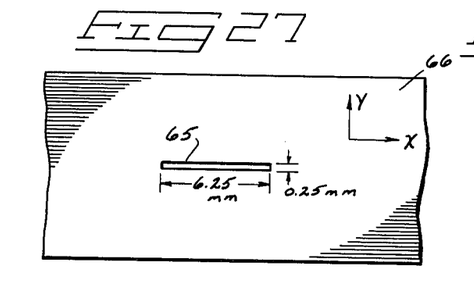
FIG. 27 is a plan view of the test procedure in FIG. 26.
Figure 28:
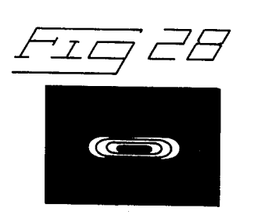
FIG. 28 illustrates the fringe patterns which resulted from the test procedure shown in FIGS. 26 and 27.
Figure 29:
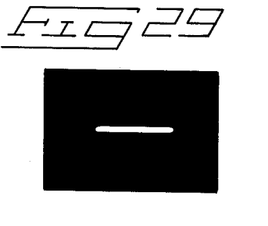
FIG. 29 is a reconstructed image developed from the fringe patterns of FIG. 28.
Figure 30:
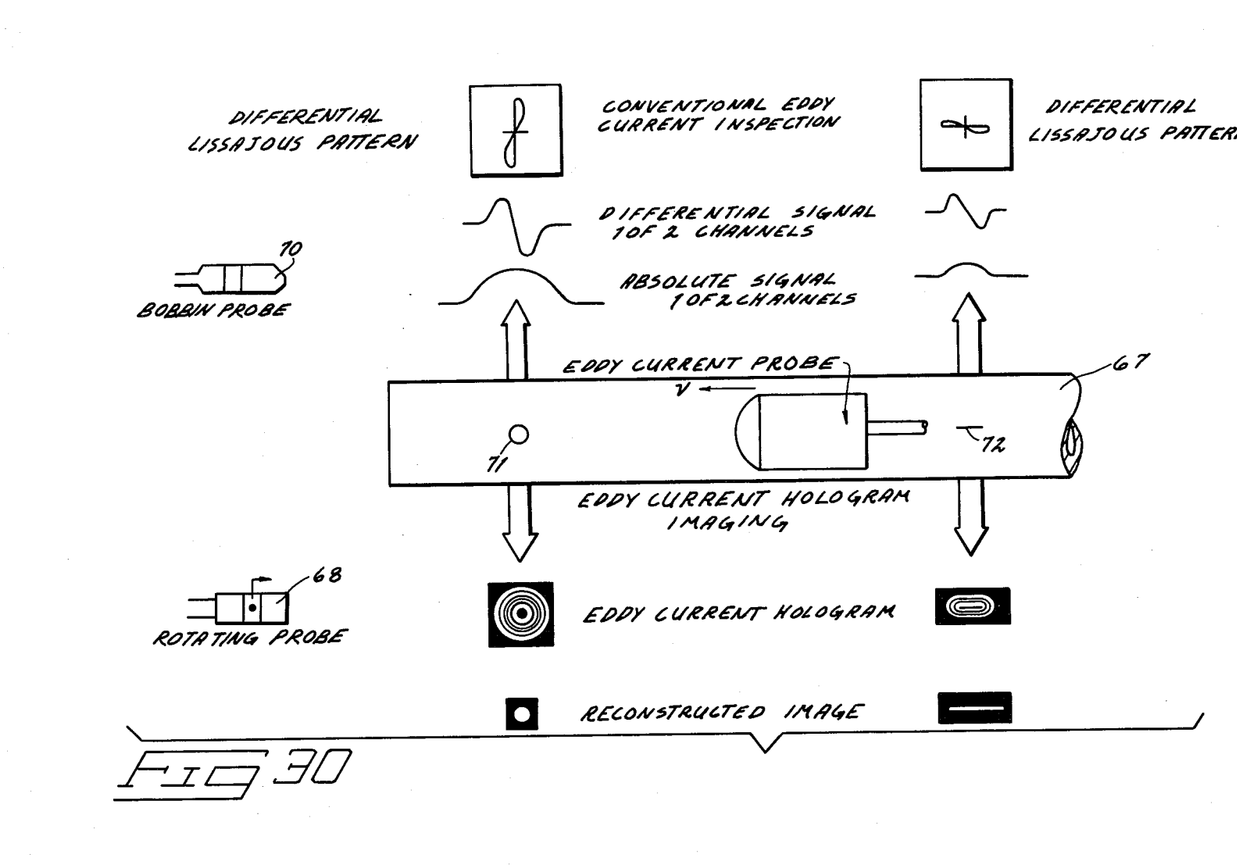
FIG. 30 is a schematic comparison of conventional eddy current techniques and the present invention.

Reconstruction of the synthetic electromagnetic or acoustic hologram to produce an optical image of a detected flaw can be accomplished by a simple optical computer as shown in FIG. 8. A laser 50 provides the coherent source light to illuminate and reconstruct the synthetically developed hologram mounted within a liquid gate 51. The spatial filter 52 shapes or filters the beam from laser 50 to ensure that the light source approaches a point source. The apparatus should include a mechanical or electronically timed shutter which provides the necessary light exposure when photographing the flaw images for permanent records. The adjustable mechanical aperture 53 provides the required light over the entire area of the hologram. The position of lens 54 is variable. Moving lens 54 brings the true or real image of the flaw into focus on the viewing screen 55. Different lens positions corresponds to different flaw depths in the test sample.

The hologram is shown within a liquid gate 51 containing a solution with an index of refraction approximating that of the hologram film. The liquid gate essentially eliminates the undesired effects of film thickness variations which would otherwise result in phase errors. The solution surrounds the film between two optical flats, making the film appear as thick as the width of the gate to the coherent light. The optical smooth surfaces now represent the film surfaces, thus eliminating present technique of phase multiplication holography provides two dimensional image that show the unique defect geometries. This should greatly enhance the interpretation analysis for the test procedures and substantially reduce the required operator training.

The foregoing description of a preferred embodiment of the invention has been presented for purposes of illustration and description. It is not intended to be exhaustive or to limit the invention to the precise form disclosed, and obviously many modifications and variations are possible in light of the above teaching. The embodiments discussed in detail were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

We claim:

1. A method of non-destructive testing for identifying internal structural characteristics of an object, comprising:
   penetrating the object by waveform radiation from an excitation signal of constant frequency;
   scanning the object to produce an output signal of said constant frequency and of varying phase value as a function of the internal structural characteristics of the object;
   multiplying the phase values and frequency of the output signal by a preselected number;
   detecting phase differences between the multiplied phase values of the output signal at the multiplied frequency and the phase values of the excitation signal after multiplication of its frequency by said preselected number;
   recording a two dimensional fringe pattern by producing a scanned plot of the object as a function of the detected phase differences between the two multiplied frequency signals; and
   reconstructing the fringe pattern by holographic techniques to produce a visual image of the internal structural characteristics of the object.

2. A method as set out in claim 1 wherein the object is metallic and the radiation is electromagnetic.

3. A method as set out in claim 1 wherein the output signal is derived from eddy currents generated within the object as a result of its penetration by the waveform radiation.

4. A non-destructive testing apparatus for identifying internal structural characteristics of an object, comprising:
   scanning means for penetrating the object by waveform radiation from an excitation signal of constant frequency and for generating an output signal of constant frequency which varies in phase value as a function of the internal structural characteristics of the object encountered by the radiation;
   phase multiplier means for multiplying the frequency and phase values of the output signal by a preselected number;
   reference means operatively connected to said scanning means for producing a reference excitation signal by multiplying the constant frequency of said scanning means by said preselected number;
   means for detecting phase differences between the multiplied output signal and the reference excitation signal;
   plotting means for producing a two dimensional fringe pattern of internal structural characteristics of the object by recording a scanned plot of the object as a function of detected phase differences between the multiplied output signal and the reference excitation signal; and
   means for reconstructing the fringe pattern by holographic techniques to produce a visual image of the internal structural characteristics of the object.

5. An apparatus as set out in claim 4 wherein said phase multiplier means is a phase locked loop having an input connected to said scanning means and an output connected to said means for detecting phase differences.

6. An apparatus as set out in claim 4 wherein said scanning means is a coil responsive to eddy currents generated in the object as a result of its penetration by electromagnetic radiation.

7. A nondestructive testing apparatus for monitoring internal structural characteristics of an object, comprising:
   means for causing radiation at a known frequency to penetrate the object;
   scanning transducer means within a fixed plane relative to the object for producing an output signal at said known frequency as a result of such penetration, the phase values of the output signal being a function of the internal structural characteristics of the object encountered by the radiation;
   phase multiplier means operably connected to said transducer means for multiplying both the frequency and the phase values of the output signal by a preselected number;
   means for multiplying the known frequency of the radiation penetrating the object to produce a reference signal;
   phase detector means for producing a variable write signal as a function of detected changes in the phase values of the multiplied output signal with respect to the reference signal;
   storage display means operably connected to said scanning transducer and to said phase detector means for producing a fringe pattern representative of the internal structural characteristics of the object in the form of a mechanical two dimensional scan display that is a function of the variable write signal; and
   means for reconstructing the fringe pattern by holographic techniques to produce a visual image of the internal structural characteristics of the object.

8. An apparatus as set out in claim 7 wherein the scanning transducer means is of a type which detects output signals from a point source.

* * * * *